United States Patent [19]

Huang

[11] Patent Number: 4,957,735
[45] Date of Patent: * Sep. 18, 1990

[54] TARGET-SENSITIVE IMMUNOLIPOSOMES- PREPARATION AND CHARACTERIZATION

[75] Inventor: Leaf Huang, Knoxville, Tenn.

[73] Assignee: The University of Tennessee Research Corporation, Knoxville, Tenn.

[*] Notice: The portion of the term of this patent subsequent to Nov. 24, 2004 has been disclaimed.

[21] Appl. No.: 12,321

[22] Filed: Feb. 9, 1987

Related U.S. Application Data

[63] Continuation-in-part of Ser. No. 816,817, Jan. 7, 1986, abandoned, which is a continuation-in-part of Ser. No. 619,844, Jun. 12, 1984, Pat. No. 4,708,933.

[51] Int. Cl.$^5$ ............... A61K 9/50; A61K 39/42; A61K 39/44
[52] U.S. Cl. ............... 424/85.8; 424/85.91; 424/86; 424/427; 424/450; 436/829; 530/389; 530/390
[58] Field of Search ............... 264/4.1, 4.3, 4.6; 424/85, 86, 87, 85.8, 85.91, 86, 427, 450; 436/829; 530/389, 390

[56] References Cited

U.S. PATENT DOCUMENTS

| | | | |
|---|---|---|---|
| 3,887,698 | 11/1975 | McConnell | 436/528 |
| 4,193,983 | 3/1980 | Ullman et al. | 424/12 |
| 4,235,792 | 11/1980 | Hsia et al. | 260/403 |
| 4,342,739 | 8/1982 | Kakimi et al. | 436/829 |
| 4,342,826 | 8/1982 | Cole | 435/7 |
| 4,372,745 | 2/1983 | Mandle et al. | 436/537 |
| 4,480,041 | 10/1984 | Myles et al. | 436/508 |
| 4,483,921 | 11/1984 | Cole | 435/7 |
| 4,517,303 | 5/1985 | Freytag et al. | 436/501 |
| 4,668,638 | 5/1987 | Janoff et al. | 264/4.6 |
| 4,671,958 | 6/1987 | Rodwell et al. | 424/86 |
| 4,708,933 | 11/1987 | Huang et al. | 436/829 |
| 4,731,324 | 3/1988 | Huang et al. | 436/520 |
| 4,789,633 | 12/1988 | Huang et al. | 435/240.2 |

FOREIGN PATENT DOCUMENTS

WO80/01515 1/1980 PCT Int'l Appl.
WO83/03473 3/1983 PCT Int'l Appl.

OTHER PUBLICATIONS

Ho et al., *Journ. Immunol.*, 134, 4035–4040, 1985.
Ho et al, *Biochemistry*, 25, 5500–5506, 1986.
Huang et al, *Journ. Biol. Chem.*, 255, 8015–8018, 1980.
Petrossian et al., *Biochimica et Biophysica Acta. (1984)*: 217–227.
Alving et al., *Biochemistry* 8 (1969): 1582.
Kinsky et al., *Biochemistry* 8 (1969): 4149.
Alving et al., *Liposomes* (Marcel Dekker 1983): 209–287.
Szoka et al., *Annual Rev. Biophys. & Biogen.* 9 (1980): 467.
Deamer et al., *Liposomes* (Marcell Dekker 1983): 27–51.
Reiss-Husson, *Journal of Molecular Biology* 25 (1967): 363.
Rand et al., *Chem. Phys. Lipids* 6 (1971): 333.
Enoch et al., *PNAS* 76 (1979): 145.
Eisen et al., *Meth. Immunology Immunochemistry* 1 (1967): 351.
Warr, *Antibody As A Tool* . . . (Wiley, 1982): 59–96.

*Primary Examiner*—Robert J. Warden
*Assistant Examiner*—David A. Saunders
*Attorney, Agent, or Firm*—Ernest V. Linek; George W. Neuner

[57] ABSTRACT

Novel target-sensitive immunoliposomes were prepared and characterized. In this invention, target specific binding of antibody-coated liposomes was sufficient to induce bilayer destabilization, resulting in a site-specific release of liposome contents.

Unilamellar liposomes were prepared by using a small quantity of palmitoyl IgG (pIgG) to stabilize the bilayer phase of the unsaturated phosphatidylethanol amine (PE) which by itself does not form stable liposomes. A mouse monoclonal IgG antibody to the glycoprotein D (gD) of Herpes Simplex Virus (HSV) and dioleoyl PE were used in one preferred embodiment.

In another preferred embodiment, potentially cytotoxic antiviral drugs were entrapped in target sensitive (TS) immunoliposomes and delivered to HSV infected cells. Potency was as much as 1000 times superior to the free drug and cytotoxicity was decreased by as much as 3000 fold.

20 Claims, 9 Drawing Sheets

TARGET-SENSITIVE IMMUNOLIPOSOMES-PREPARATION AND CHARACTERIZATION

CROSS REFERENCE TO RELATED APPLICATIONS

This application is a continuation-in-part of copending application Ser. No. 816,817, filed Jan. 7, 1986 now abandoned, which in turn is a continuation-in-part of copending application Ser. No. 619,844, filed June 12, 1984 now U.S. Pat. No. 4,708,933, the disclosures of which, to the extent necessary, are hereby incorporated herein by reference.

BACKGROUND OF THE INVENTION

Target-specific liposomes have been studied extensively for their use as inert carriers for drugs, enzymes, hormones, DNA and other biomedically important substances (for recent reviews see Connor et al., *Pharm Ther.*, 28: 341-365 (1985). Immunoliposomes have been shown to bind specifically to their target cells in vitro and in vivo. The subsequent events which follow cell binding are currently of great interest since liposome binding may not necessarily be followed by the delivery of the encapsulated drug into the target cell.

One approach to ensure target-specific delivery of drugs into the cell is to fuse liposomes with intact cells. This approach has been demonstrated using a variety of fusogens such as Sendai virus (Okada, *Exp. Cell Res.*, 26: 98-107 (1962), Nakanishi et al., *Exp. Cell Res.*, 159: 399-409 (1985)); synexin (Hong et al., *Proc. Natl. Acad. Sci. U.S.A.*, 79: 4642-4644 (1982)); and polyethyleneglycol (Boni et al., *Biochem. Biophys. Acta.*, 775: 409-418 (1984), as well as fusion by means of pulsed electric field (Vienken & Zimmerman, *FEBS Letts.*, 182: 278-280 (1985).

However, all of these fusion protocols suffer from a relatively high cytotoxicity to the target cells. An alternative approach for drug intake is to exploit cellular endocytosis. Using pH-sensitive immunoliposomes, which become fusion competent at pH below 6.5 and fuse with endosomes, this approach was successful for cytoplasmic delivery of antitumor drugs (Connor & Huang, *J. Cell Biol.*, 101: 582-589, (1985). However, an endocytosis-dependent drug delivery system may not be applicable to target cells with low endocytotic activity.

To overcome this constraint, heat-sensitive immunoliposomes were developed (Sullivan & Huang, *Biochim. Biophys. Acta.*, 812: 116-126 (1985). This cell delivery system depends on the uptake of drug released from briefly heated cell bound liposomes. For example, enhanced uptake of $^3$H-uridine encapsulated in heat-sensitive immunoliposomes composed of dipalmitoyl phosphatidylcholine (DPPC) was reported recently (see for example, Sullivan & Huang, *PNAS USA*, 83:6117-6121 (1986)).

Although this heat-sensitive system was quite efficient, the localized heating of liposome treated cells may not be feasible for many applications, particularly in vivo situations.

SUMMARY OF THE INVENTION

The present invention is thus directed to another approach in the design of liposomes with a built-in mechanism to release encapsulated drugs at the surface of the target cell.

The target-sensitive (TS) immunoliposomes of the present invention require, an antibody not only for specific target cell recognition but also to stabilize the otherwise unstable liposomes.

In preferred embodiments, the antibody of choice is immunoglobulin G or IgG. Since the IgG antibody is not sufficiently hydrophobic to be incorporated into the liposome membrane (Huang & Kennel, *Biochemistry*, 18: 1702-1707 (1979)), palmitic acid was covalently coupled to IgG (Huang et al., *J. Biol. Chem.*, 255: 8015-8018 (1980)) and palmitoyl IgG was used to prepare the TS immunoliposomes.

Unsaturated phosphatidylethanolamine (PE), which does not form stable bilayers under physiologic conditions (Gruner et al. *Ann. Rev. Biophys. Biophyschem.*, 14: 211-238 (1985); Cullis and DeKruijff, *Biochim. Biophys. Acta.*, 559: 399-420 (1979)), can be made to do so in a variety of ways.

These have included mixing with another type of lipid such as dinitrophenylcaproyl PE (Ho & Huang, *J. Immunol.*, 134: 4035-4040 (1985)); N-succinyldioleoyl PE (Naar & Schroit, *Biochemistry*, 24: 5967-5971 (1985)) or various types of mixed-lipids (for a review see Cullis & DeKruijff, supra); fatty acids and derivatives such as oleic acid (Duzgunes et al., *Biochemistry*, 24: 3091-3098 (1985) and Huang & Liu, *J. Biophys.*, 45: 72a (1984)), cholesterol hemisuccinate (Ellens et al., *Biochemistry*, 23: 1532-1538 (1984)) and palmitoyl-homocysteine (Connor et al., *Proc. Natl. Acad. Sci. USA*, 81: 1715-1718 (1984)), and finally proteins such as glaycophorin A (Taraschiet al., *Biochemistry*, 21: 5756-5764 (1982); Ho & Huang, supra).

In the preferred embodiment a fully acylated IgG antibody is shown to stabilize the otherwise unstable PE liposomes. Upon binding with a multivalent target which expresses antigen, the liposome destabilizes and releases its contents. This now type of liposome is called a "target sensitive immunoliposome," or "TS immunoliposome."

The TS immunoliposome-encapsulated and free cytotoxic drugs of nucleoside analogs cytosine-beta-D-arabinoside (AraC) or acycloguanosine (acyclovir, ACV) were compared for their antiviral efficacy and cell toxicity.

When the mouse fibroblast L929 cells were infected at low multiplicity with herpes simplex virus (HSV), AraC encapsulated in TS immunoliposomes composed of transphosphatidylated egg phosihitidylethanol amine (TPE) effectively inhibited virus replication and had far less cell cytotoxicity than the corresponding free drug.

As a measure of cytotoxicity, the drug concentration required to inhibit 50% of [$^3$H]dT incorporation 42 hr. later ($CD_{50}$) was determined. For free AraC, this value was 0.3 ng/ml, whereas for TS immunoliposome encapsulated AraC, the $CD_{50}$ exceeded 1 ug/ml. However, TS immunoliposome encapsulated AraC was virus inhibitory (50% effective dose=$ED_{50}$) at 1.8 ng/ml. A free drug concentration of at least 1000 fold greater was required for comparable antiviral activity. A similar phenomenon was observed when ACV was administered via TS immunoliposomes. The $CD_{50}$ of the free and TS immunoliposomes encapsulated ACV was 12.5 ng/ml and 1.4 ug/ml respectively, while the $ED_{50}$ of the free and TS immunoliposomes encapsulated ACV was 1.1 ug/ml and 125 ng/ml, respectively.

Consequently, the TS-immunoliposomes are superior drug delivery vehicles, especially when drugs are cytotoxic to cells. The use.,of liposomes of the target insensitive variety provided some enhancement of activity, but this was several fold less than that observed with TS immunoliposomes.

BRIEF DESCRIPTION OF THE DRAWINGS

FIG. 3 illustrates the binding of immunoliposomes to L cells. Uninfected (oc, cc), HSV-infected (to, ct, ob, cb) L cells were incubated with varying amount of PE liposomes (oc, ot, ob) and PC liposomes (cc, ct, cb). The amount of lipid (A) and IgG (B) bound to the cell was plotted against the amount of lipid and IgG added in the form of immunoliposomes Twenty micro-g of free anti-HSV-gD-IgG was used to block PE (ob) and PC (cb) immunoliposomes binding to the HSV-infected L cells.

FIG. 4 illustrates the cell-induced lysis of immunoliposomes. To uninfected oc, cc), HSV-infected (ot, ct, oc), or Sendai virus infected (ob) L cells in suspension was added 0.58 nmol of calcein-encapsulated PE (ot, ct, oc, ob) or PC (cc) immunoliposome. To inhibit the lysis of PE immunoliposomes by HSV-infected L cells, 1.8 nmoles of PC immunoliposomes containing no calcein were also added (ot).

"Infect" refers to the state of infection of the cell by HSV, i.e., "+" cells are infected; "−" cells are not;

"AraC" a "+" symbol represents presence of the drug cytosine-beta-D-arabinoside (free drug); the "−" symbol represents absence thereof;

"(Ab:TPE)" a "+" symbol represents the presence of the drug cytosine-beta-D-arabinoside, encapsulated in TS-immunoliposomes composed of TPE and palmitoyl-anti-HSV-gD-IgG; while a "−" symbol represents each the lack thereof; and "(EPC)" a "+" symbol represents the presence of a liposome composition containing egg PC and no antibody; while a "−" symbol represents each the lack thereof.

Figure 8A:
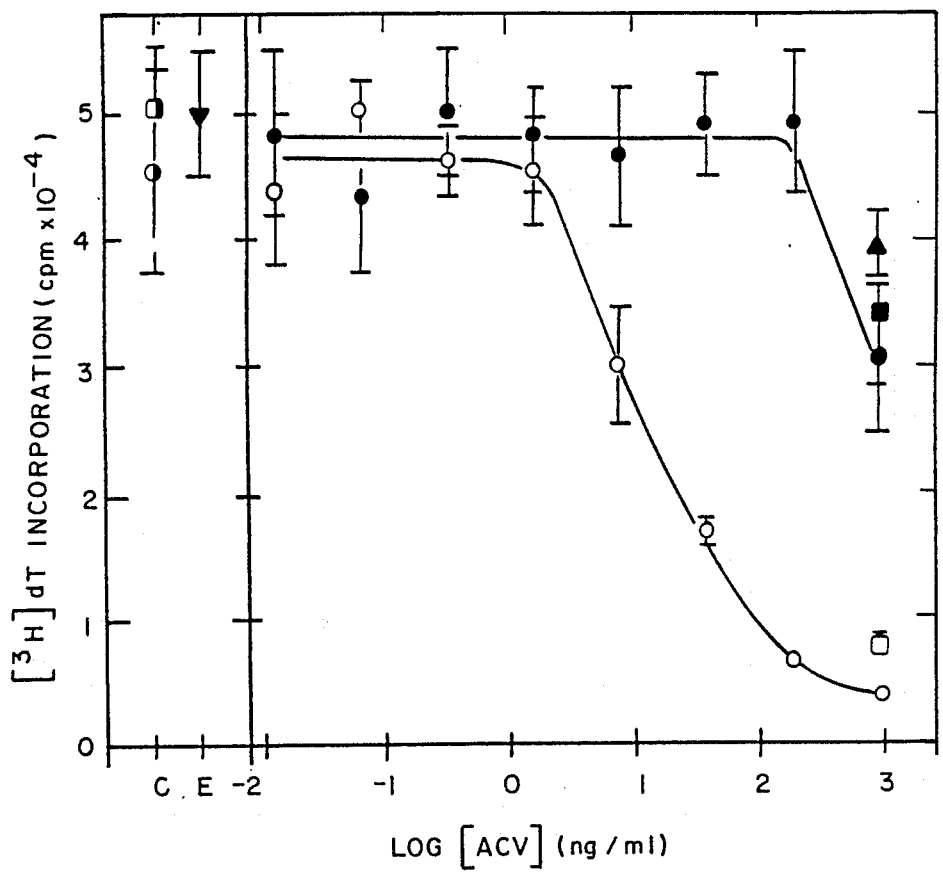

FIGS. 8(A) and (B) compare the effects of encapsulated ACV on HSV-infected L929 cells. In these Figures, the following definitions apply;

"Infect" refers to the state of infection of the cell by HSV, i.e., "+" cells are infected; "−" cells are not;

"ACV" a "+" symbol represents presence of the drug acyclovir (free drug); while the "−" symbol represents absence thereof;

"(Ab:TPE)" a "+" symbol represents the presence of the drug acyclovir, encapsulated in TS-immunoliposomes composed of TPE and palmitoyl-anti-HSV-gD-IgG; while a "−" symbol represents each the lack thereof; and "(EPC)" a "+" symbol represents the presence of a liposome composition containing egg PC and no antibody; while a "−" symbol represents each the lack thereof.

Figure 9A:
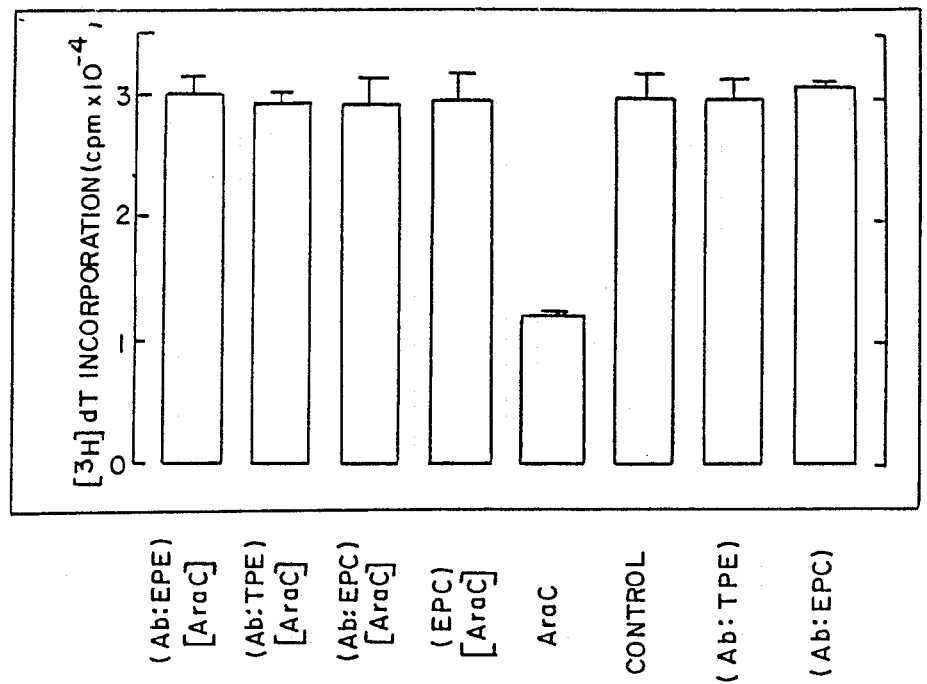

FIGS. 9(A) and (B) represent the data from studies of virus replication versus various liposome compositions.

In these Figures, the following definitions apply; "Ab:EPE/[AraC]" represents TS immunoliposomes composed of egg phosphatidyl ethanol amine, targeted with antibody and containing AraC; "Ab:TPE/[AraC]" represents TS immunoliposomes composed of transphosphorylated phosphatidylethanol amine, targeted with antibody, and containing AraC; "Ab:EPC/AraC" represents TS immunoliposomes composed of egg phosphatidyl choline, targeted with antibody and containing AraC; "EPC/[AraC]" represents untargeted (non-immuno) liposomes composed of egg phosphatidyl choline, containing AraC; "AraC" represents free drug; "control" represents empty liposomes; while "Ab:TPE" and "Ab:EPC" represent targeted liposomes, without encapsulated drug.

Figure 10:
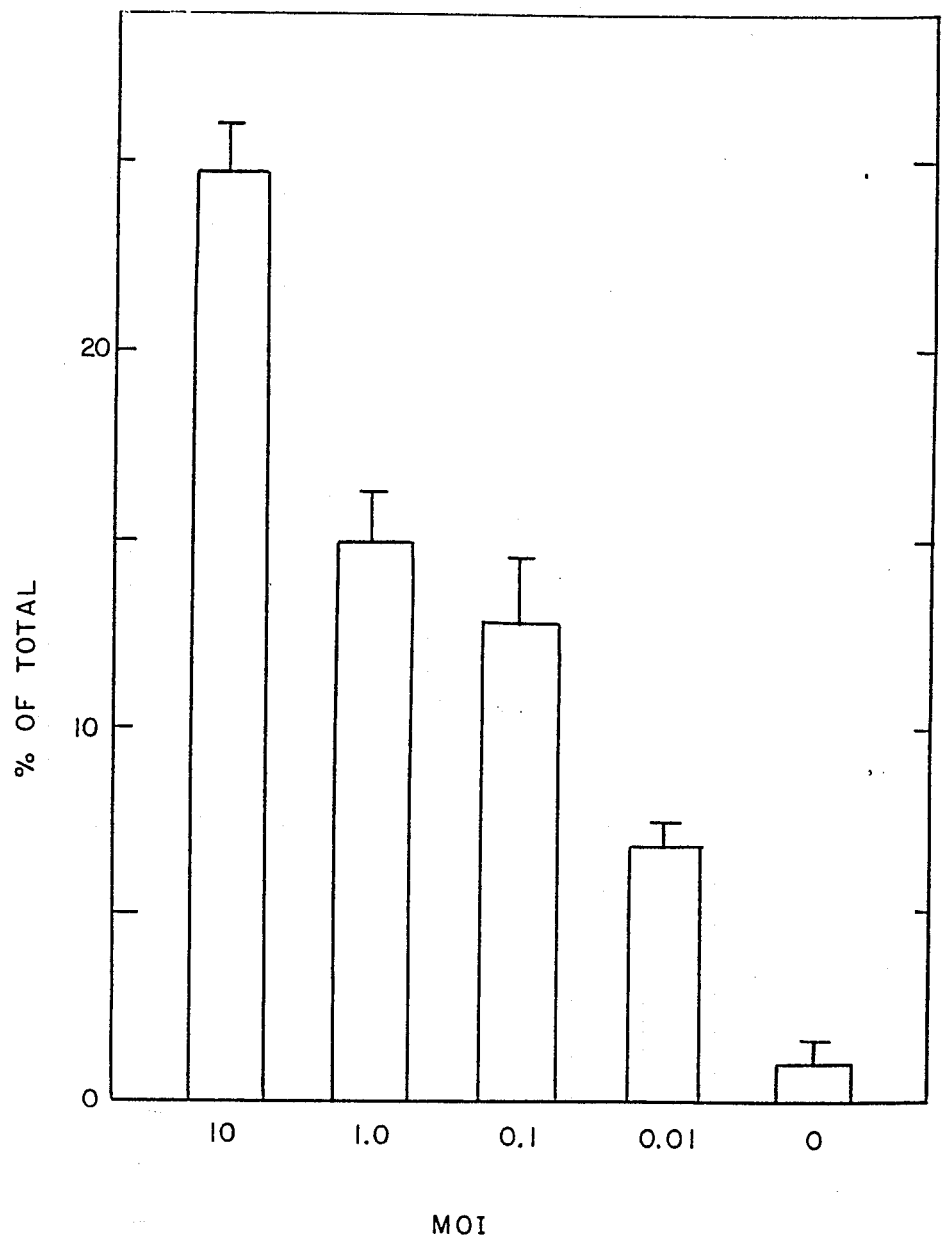

FIG. 10 illustrates the multiplicity of infection (MOI) dependency of the cell induced release of [$^3$H]AraC from the TS immunoliposomes of the present invention.

DETAILED DESCRIPTION OF THE PREFERRED EMBODIMENTS

According to the "hydration" theory (Marcvelja & Radic, *Chem. Phys. Lett.*, 42: 129–130 (1976), PE, which has a relatively low head-group charge content, will not attract a significant number of water molecules at neutral pH. This results in a small head group (Rand et al., *Chem. Phys. Lipids*, 6: 333–342 (1971); K. Harlos, *Biochim. Biophys. Acta*, 511: 348–355 (1978)) that gives an average dynamic shape of an inverted cone (Israelachvili et al., *Quart. Rev. of Biophys.*, 13: 121–200 (1980)).

To maintain bilayer structure, PE requires complementary molecules which assume a dynamic truncated cone or wedge shape. The membrane-bound pIgG in our system probably complements the inverted cone-shaped PE by a combination of attracting interfacial water, due to the hydrophilic Fab portion at the bilayer surface, and the intrinsic molecular conformation of pIgG that gives the average dynamic shape of a truncated cone.

In addition, membrane bound pIgG may serve as a repulsion force against the PE bilayer contact, thereby preventing the already formed PE bilayer reverting to the hexagonal phase.

It is also interesting to note that only five pIgG molecules were required to stabilize a 500A PE liposome. For glycophorin-PE liposomes of comparable size, 100 molecules of glycophorin were required for bilayer stabilization (Taraschi et al., supra and Ho & Huang, supra), indicating that the Fab portion attracts more interfacial water to the bilayer surface. Hence, the pIgG exhibit a markedly higher degree of stabilizing activity on PE bilayers than does glycophorin.

Figure 4:
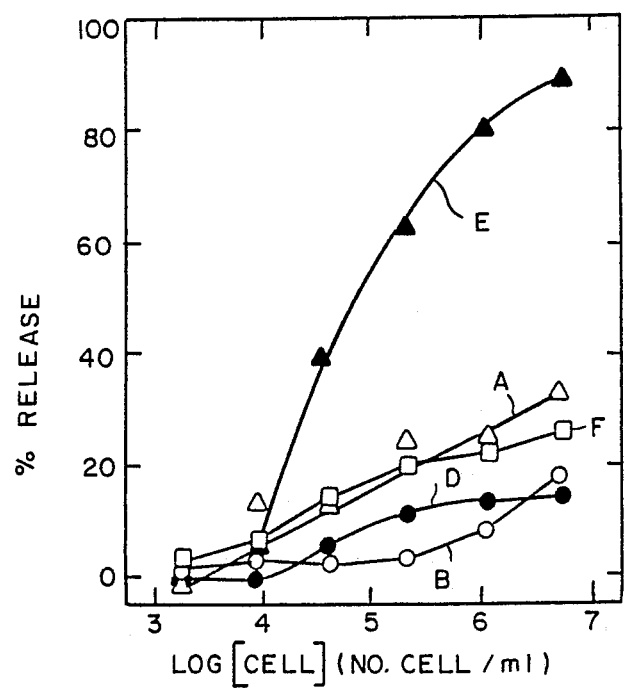

Data presented herein clearly demonstrate that PE immunoliposomes can be destabilized upon specific binding to target cells (FIG. 4). Although the detailed molecular mechanism of target cell-induced destabilization of immunoliposomes requires definition, they probably involve a lateral phase separation of the liposome membrane components.

The exact stabilization mechanism of the PE bilayer by palmitoyl antibody is not known at present. However, the orientation of pIgG in the bilayer is probably a major contributing factor. The preferential derivitization of palmitic acid to the Fc region (70%) of the IgG indicates that either the Fc-linked palmitic acids or the acylated Fc of the antibody is inserted into the bilayer wi region outside and available for binding (FIG. 6).

Although the extent of the insertion is not known, the destabilization immunoliposomes by papain, which cleaves the of IgG (FIG. 5), clearly demonstrates that an Fab domain is essential for stabilization o PE bilayers. Since the hinge region is available for papain cleavage, the Fab portion of the pIgG is likely exposed to the aqueous phase.

Figure 3A:
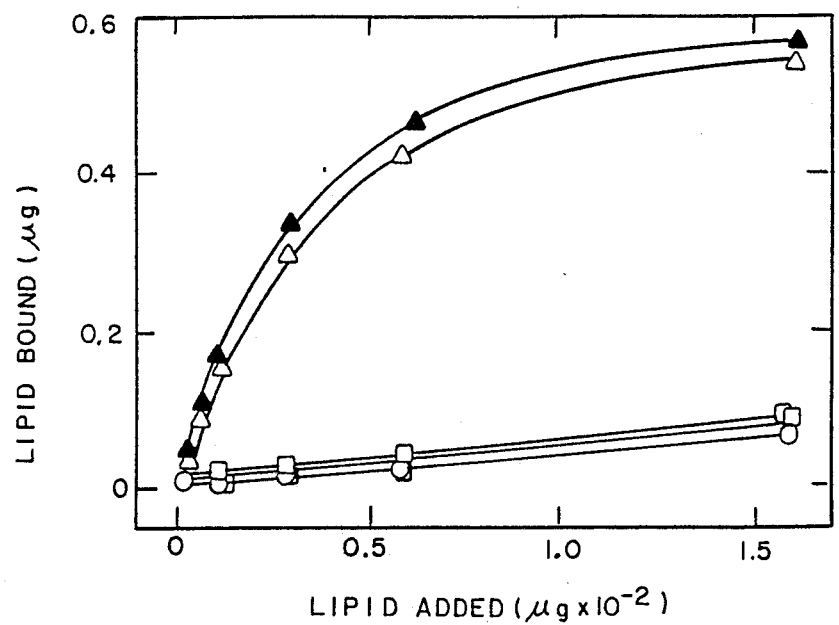
In FIGS. 3 and 4, the following definitions apply; all open symbols (oc=circles; os=squares; ot=triangles; ob=boxes) represent phosphitidyl ethanol amine (PE) derived liposomes; and all closed symbols (cc=circles; cs=squares; ct=triangles; cb=boxes) represent phosphitidyl choline (PC) derived liposomes.
Figure 3B:
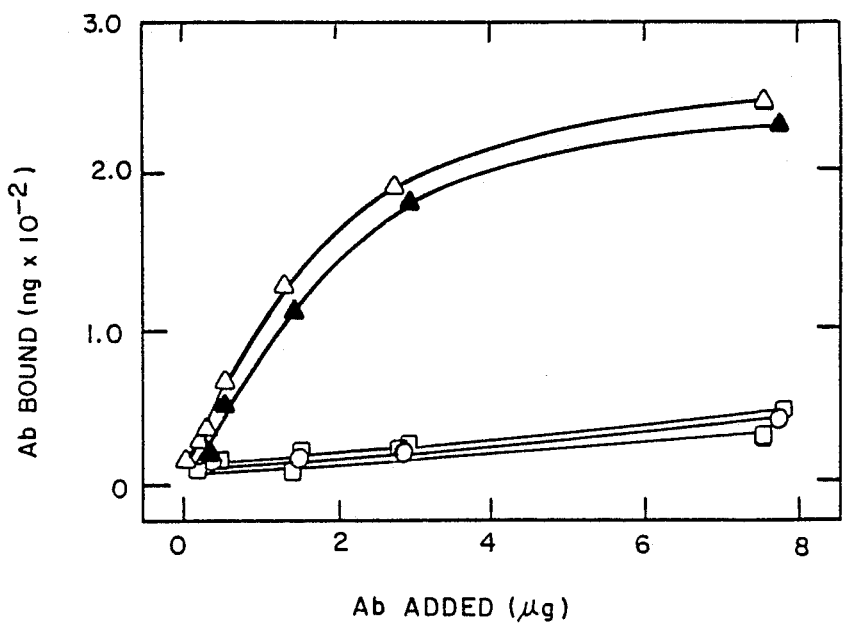

This is further supported by the experimental finding that the Fab portion of the liposome bound pIgG is available for antigen binding with an apparent $K_d$ approximately the same as that of the native IgG (Table 1 and FIG. 3). The present model of stabilization is also consistent with the physical principles involved in membrane organization.

Figure 6:
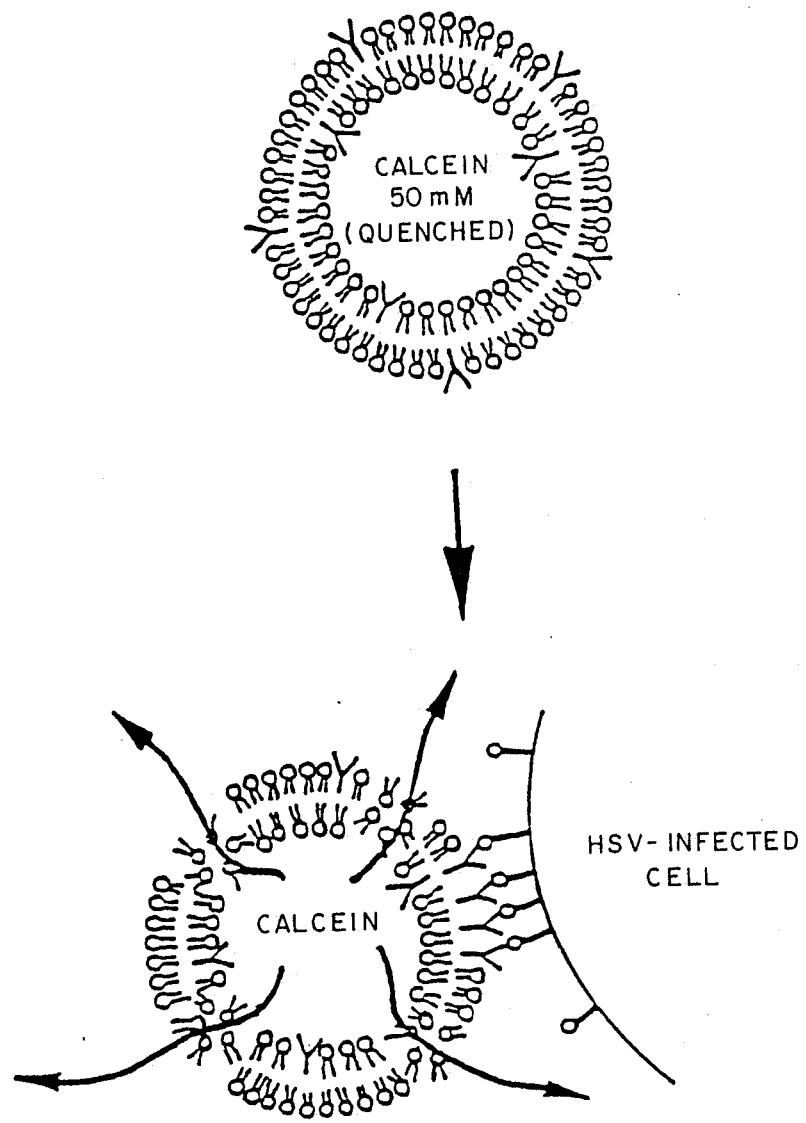
FIG. 6 is a schematic representation of the specific lysis of the target-sensitive immunoliposomes.

As schematically presented in FIG. 6, pIgG molecules are likely to freely diffuse in the fluid bilayer with a diffusion coefficient of $1.87 \times 10^{-8}$ cm$^2$/sec. (Huang, *Biochemistry*, 24: 29-34 (1985). Consequently, only a fraction of a second is required for the surface bound pIgG to diffuse to the contact area between liposome and cell.

This process eventually causes a multiple immune complex formation at the contact area (contact capping), Bell, *Physical Chemical Aspects of Cell Surface Events in Cellular Regulation*, (Delisi, and Blumenthal, eds.) Elsevier/North-Holland, N.Y., (1979)). As a result of lateral phase separation, the effective concentration of pIgG in the bulk lipid bilayer decreases resulting in liposome destabilization.

Although this hypothesis remains speculative, it is consistent with our previous finding that multivalent antibody-binding is essential for lysis of antigen stabilized PE liposomes.

In addition to lateral phase separation of bilayers, contact between the individual PE immunoliposomes is probably required for the destabilization of the PE bilayer (Ellens et al., supra). This contact requirement could be satisfied either by collision between adjacent liposomes bound to the same cell or between liposomes on separate cells. Although the kinetics of this process remains to be investigated, the overall destabilization rate of the TS immunoliposomes is likely dependent on collision rate which controls the formation of the immune complex between a TS immunoliposome and a target cell.

The possibility of a hexagonal (H$_{II}$) phase intermediate in the destabilization of TS immunoliposomes should not be overlooked, because a similar phenomenon has been observed by Taraschi et al., supra. When lectins were added to glycophorin A-stabilized PE bilayer, extensive hexagonal phase formation was detected.

Potential use of the target-sensitive immunoliposomes as a site-specific drug delivery system depends on the following considerations. First, the target cell must express a sufficient antigen density to promote contact capping of the liposome following binding. Second, the drug released from liposomes at the cell surface should be rapidly taken up by the target cell. Cytotoxic and antiviral drugs of nucleoside analogs such as fluorodeoxyuridine, iododeoxyuridine, acyclovir or cytosine arabinoside are good choices (Plagemann and Wholhueter, *Current Topics in Membrane and Transport*, 14: 226-330 (1980)).

For the present invention, nucleoside analogs of anti-HSV drugs, such as iododeoxy-uridine and acyclovir, should serve the same purpose. Thus, selective uptake of the antiviral drugs by the infected cells could be mediated by the TS immunoliposomes described herein. Since drug delivery by TS immunoliposomes depends only on antigen-antibody binding, there is no additional requirement of the target cell metabolism such as endocytosis.

Accordingly, this targeting design can be effective for cells that do not actively endocytose as long as sufficient antigen density and functional drug transporters are available at the cell surface.

In principle, any immunoglobulin that is monospecific for the target antigen can be used to prepare the TS immunoliposomes. Furthermore, one would expect that TS immunoliposomes lyse when binding occurs with other types of multivalent antigens such as intact viruses, bacteria and other pathogens. If a suitable reporter molecule is encapsulated in the liposome, a simple liposome-based immunoassay could be designed.

TABLE 1

| Derivatization of anti-HSV-gD-IgG with palmitic acid | | |
|---|---|---|
| Input molar ratio NHSP/IgG (mol/mol) | Coupling stoichiometry, Palmitic Acid/IgG (mol/mol) | $K_d$ ($\times 10^8$ M) |
| 0 | 0 | 0.75[a] |
| 11 | 1.4 | ND[b] |
| 14 | 2.1 | ND |
| 20 | 2.2 | 1.17 |
| 25 | 5.15 | ND |
| 30 | 6.66 | ND |
| 44 | 14.6 | 1.90 |

[a]$K_d$ for native anti-gD-IgG was $0.48 \times 10^{-8}$ M.
[b]not determined

The degree of palmitic acid coupling to the IgG has been studied by varying the input ratio of $^3$H-NHSP to $^{125}$I-IgG from 0 to 44. The final molar ratio of palmitic acid to IgG was determined from the pooled IgG fractions (void volume) of a Sephadex G75 column (Huang et al., *Biochim. Biophys. Acta.*, 716: 140-150 (1982)).

These values represent the average ratio since the pooled samples contained both derivatized and underivatized antibodies. As can be seen in Table 1, increasing input ratio of NHSP/IgG resulted in more palmitic acid coupled per IgG without significant change in the antigen binding affinity as revealed by the dissociation constant $K_d$ of the antibody.

Therefore the coupling condition was sufficiently mild and the coupling stoichiometry can be controlled by varying the input NHSP/IgG ratio. To determine the palmitic acid distribution on the pIgG we used papain to cleave a pIgG preparation with the coupling stoichiometry of 2.2 in the presence of 0.15% DOC according to R. P. Porter, *J. Biochem.*, 73: 119-126 (1959)).

When the resulting mixture was subjected to SDS-PAGE, two distinct protein bands with apparent molecular weights of 32.5 kd and 25.5 kd were detected. They were identified in western blots (Burnette, supra) as Fc and Fab, respectively. By counting radioactivity of $^{32}$H-palmitic acid, the distribution of palmitic acid on Fab and Fc were determined to be approximately 30% and 70%; respectively.

Formation of stable liposomes was monitored by their ability to encapsulate 50 mM self-quenching fluorescence dye, calcein. At this concentration, calcein fluorescence was about 70% quenched. Fluorescence was greatly enhanced as the dye was diluted upon release from liposomes. In order to determine the optimal palmitic acid to IgG coupling stoichiometry for PE liposome formation, we prepared the liposomes by sonication in the presence of 50 mM calcein with various pIgG to PE ratios for each pIgG preparation.

A wide range of coupling stoichiometry (0-14.6) was used. After chromatography to remove the untrapped dye, liposome formation was detected by analyzing the total amount of calcein encapsulated per mole of PE.

Figure 1B:
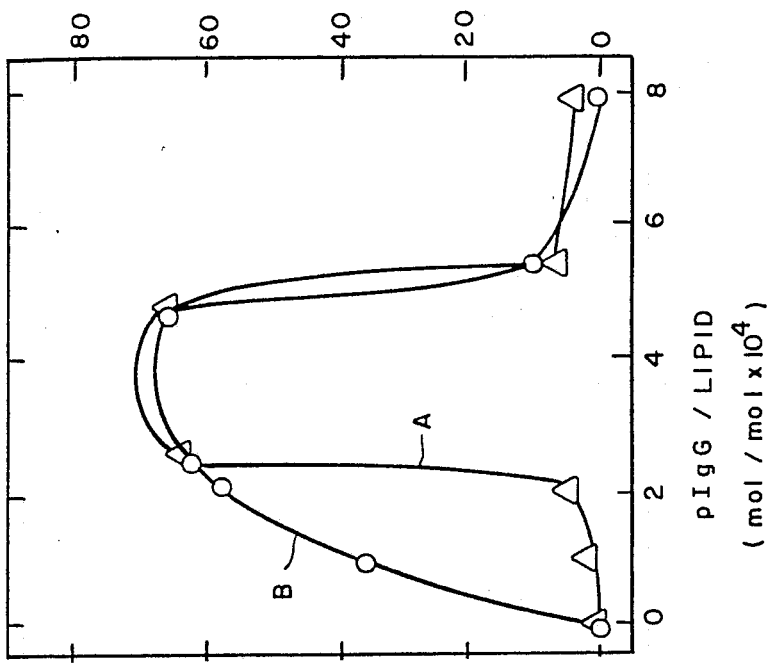
FIG. 1 illustrates the stabilization of PE liposome bilayer by palmitoyl-anti-gD-IgG. Calcein encapsulation (A) and fluorescence quenching (B) were measured with various coupling stoichiometry, palmitic acid/IgG (A), or with various pIgG to PE ratio (B).
Figure 1A:
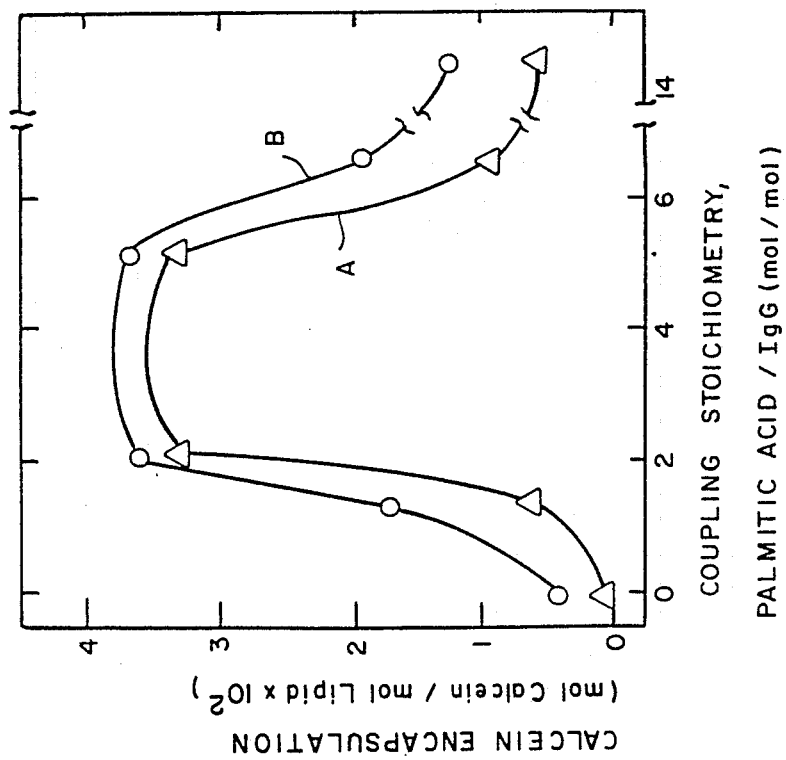

In order to demonstrate the encapsulation of calcein, quenching of calcein fluorescence was also determined (FIG. 1). As shown in FIG. 1A, we found the optimal coupling stoichiometry of palmitic acid to IgG was 2.2 to 5.1, as evidenced by the highest amount of total calcein encapsulated per mole of lipid. In this particular experiment, pIgG to lipid ratio was kept constant at $2.5 \times 10^{-4}$.

Figure 2:
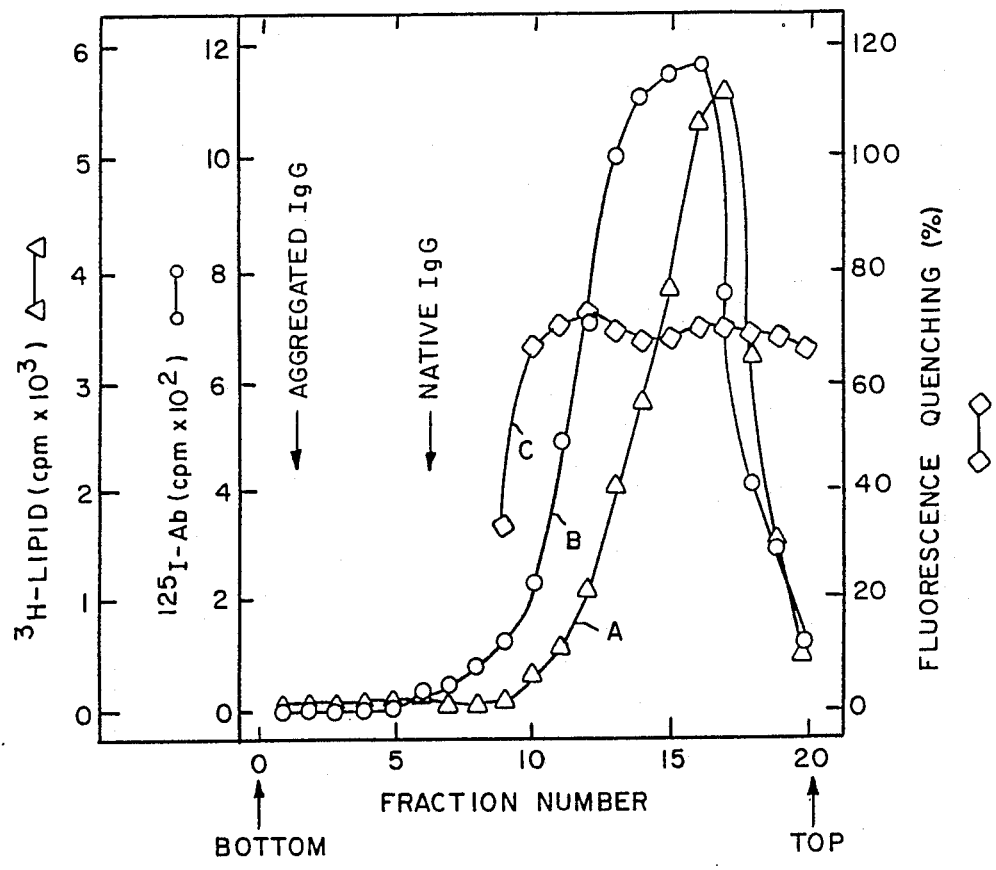
FIG. 2 represents the sucrose gradient centrifugation analysis of antibody stabilized PE liposomes. PE immunoliposomes were fractionated with 5–20% linear sucrose gradient centrifugation as described in materials and methods. Each collected fraction was analyzed for $^3$H-lipid (A), $^{125}$I-IgG (B), and fluorescence quenching (C). The arrows indicate where self-aggregated pIgG and native IgG sedimented.

These PE immunoliposomes were also analyzed by sucrose gradient centrifugation. A typical gradient profile is shown in FIG. 2. With palmitic acid to IgG coupling stoichiometry of 2.2 to 5.1, practically no underivatized IgG was detected.

In addition, the pIgG was all incorporated into the PE immunoliposome composed of pIgG:PE = 1:4,000, as evidenced by the absence of aggregated pIgG at the bottom of the gradient. Furthermore, we found heterogeneity of pIgG distribution in the liposome population. Liposomes enriched with more pIgG migrated further into the gradient than those with fewer pIgG.

For the gradient shown in FIG. 2, the pIgG:PE ratio in the population (fraction no. 13-17) was calculated to be $1.2-4.3 \times 10^{-4}$. This result indicated that the liposomes that sedimented further into the gradient contained up to 3.6 times more pIgG per mole of lipid than the ones found at the top of the gradient. However, the constant quenching of calcein fluorescence across the peak indicates that the concentration of calcein encapsulated was approximately the same, i.e. 50 mM. Therefore, despite the heterogeneity, the PE immunoliposomes prepared under the chosen conditions can stably encapsulate a small molecular weight marker, calcein.

In order to determine the optimal PE to pIgG ratio, we analyzed the calcein encapsulation and the percent quenching of the PE immunoliposomes with various ratios of pIgG to PE. In this experiment, the coupling stoichiometry of the pIgG used was 2.2.

As shown in FIG. 1B, the optimal pIgG to PE was found to 2.5 to $4.7 \times 10^{-4}$. Within the range, the highest amount of total calcein fluorescence (which was quenched up to 70%) per mole of lipid was detected. Either increasing or decreasing the pIgG to PE ratio resulted in a decrease of calcein encapsulation. With pIgG to PE ratio less than $2.5 \times 10^{-4}$, a sharp decrease was detected in the calcein encapsulation without significant decrease in quenching. This could be attributed to the heterogeneity of the liposome population. A small number of pIgG stabilized liposomes in the population could give rise to a high degree of calcein quenching. At pIgG to PE ratios greater than $4.7 \times 10^{-4}$, the excess pIgG were self aggregated as revealed by sucrose gradient centrifugation (data not shown).

These results indicate that a minimum coupling stoichiometry of 2.2 palmitic acid per IgG was required for the pIgG to stabilize the PE liposomes (FIG. 1A). In addition, the minimum pIgG to PE ratio was $2.5 \times 10^{-4}$. This combination was used to prepare the PE immunoliposomes for all subsequent experiments. Under these conditions, we calculate that liposomes of 500A average diameter have five pIgG molecules per PE immunoliposome.

Liposomes composed of pIgG:PE (1:4000) were unilamellar and the average diameter of liposomes was 500 A $\pm$130 A as determined by negative-stain electron microscopy.

In order to demonstrate the binding specificity of the immunoliposomes, mouse fibroblast L929 cells were infected with HSV and the binding of the immunoliposomes was measured at 6 hr. post infection (PI) which is the optimal time for gD expression (Cohen et al., *J. Virol.*, 36: 429-439 (1980); Balachandran et al., *J. Virol.*, 44: 334-335 (1982) and Johnson and Spear *J. Virol.*, 51: 389-394 (1984)).

By using $^3$H-CE as a lipid marker and $^{125}$I-pIgG, the binding of immunoliposomes to the cells was detected by counting $^3$H and $^{125}$I-radioactivity. With increasing concentration of liposomes added, increasing amount of both PC and PE immunoliposomes were bound specifically to the HSV-infected cells (FIG. 3).

On the contrary, very few PE or PC immunoliposomes were bound to the uninfected cells. Furthermore, the immunoliposome binding could be inhibited by preincubation of the HSV-infected cells with free IgG in three-fold excess of the highest concentration of liposome associated pIgG used.

In addition, the affinity of these immunoliposomes was measured using the Scatchard analysis (G. Scatchard, *Ann. N.Y. Acad. Sci.*, 51: 660-672 (1949). It was found that the apparent dissociation constant, $K_d$, for pIgG and lipid was $1 \times 10^{-8}$M and $4 \times 10^{-5}$M. respectively. The $K_d$ for pIgG incorporated in the immunoliposomes ($1 \times 10^{-8}$M) was very similar to the $K_d$ of free pIgG ($1.17 \times 10^{-8}$M, Table 1), indicating that significant denaturation of the antibody did not occur during the preparation of immunoliposomes.

Since no significant increase in the apparent binding affinity of antibody was observed upon incorporation into the liposomes, the binding of these liposomes to the virus-infected cells is probably not a cooperative event, see for example, Babbitt et al., supra. By comparing the apparent $K_d$ for pIgG and lipid, pIgG to lipid ratio of the cell-bound liposomes was determined to be 1:4020 (mole/mole). This finding indicates that the lipid and antibody in the liposomes were binding to cells as a unit since the pIgG to lipid ratio of the applied liposomes was 1:4000. From the X-intercept of the Scatchard plot, we had determined the maximum number of liposome bound to the HSV-infected L929 cells to be $1.3 \times 10^5$ per cell.

The ability to HSV-infected L929 cells to lyse immunoliposomes containing calcein was also investigated. As shown in FIG. 4, PE immunoliposomes were lysed specifically in a concentration dependent manner by exposure to HSV-infected cells. In contrast only partial (up to approximately 30%) lysis occurred with uninfected cells. Approximately 90% of the entrapped calcein was released at the infected cell concentration of $6 \times 10^6$ cells/ml after 30 min. incubation.

In addition, the HSV-infected cell-induced calcein release could be blocked by incubating PE immunoliposomes with a three-fold excess of the PC immunoliposomes containing no calcein. Since no significant lysis of liposomes was observed with Sendai virus-infected cells, this type of immunoliposome is target specific. Furthermore, when PC was used to substitute for PE in immunoliposomes, the lytic activity was lost.

The inability of HSV-infected cells to lyse PC containing immunoliposomes could not be attributed to the lack of liposome binding to the cells, since both the PC and PE immunoliposomes bound equally well to the HSV-infected cells (FIG. 3A and B). In order to determine whether the cell-induced increase of calcein fluorescence was due to the calcein released into the medium or into the cell, cells were pelleted and the fluorescence in the supernatant and the cell pellet were measured. Approximately 15% of total calcein was found in the pellet and the fluorescence was not quenched, indicating most of the calcein was released extracellularly.

In order to determine the essential domain of the IgG in stabilizing PE liposomes, the pIgG in calcein encapsulated PE immunoliposomes were digested with papain. Destabilization of immunoliposomes was detected by following the initial rate of calcein leakage.

Figure 5:
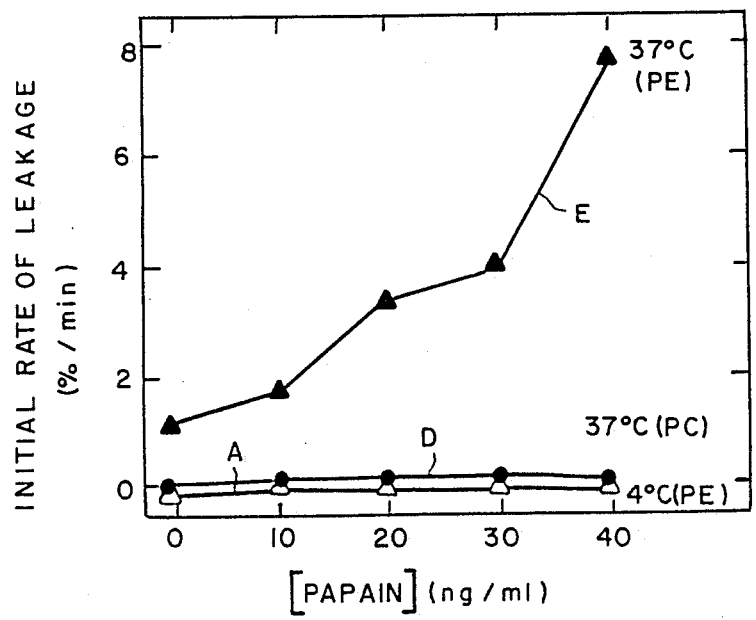
FIG. 5 illustrates the papain-induced lysis of immunoliposomes. Various concentrations of papain were added to PE (A & E) and PC (D) immunoliposomes at 37° C. (E & D) and 4° C. (E) and the initial rate of calcein leakage was measured.

With increasing concentration of papain added, elevating rate of leakage up to 8% per minute at 37° C. was observed with PE immunoliposomes (FIG. 5). This papain-induced leakage was specific for PE immunoliposomes since PC immunoliposomes were not sensitive to papain. In addition, papain-induced leakage was temperature dependent as evidenced by essentially no release of calcein from the PE immunoliposomes at 4° C. regardless of the amount of papain added.

Inability of papain to induce liposome leakage at low temperature could not be accounted for by the decrease in enzyme activity since at lease 15% activity remains when the temperature is reduced from 37° to 4° C. (Stockell and Smith, *J. Biol. Chem.*, 227: 1-26 (1957)). In addition, the papain induced leakage rate decreased as the liposomes were diluted (data not shown). This finding is in agreement with the observation of Ellens et al., supra. that destabilization of PE bilayers was concentration dependent because of the bilayer contact requirement.

We have chosen the following example to illustrate the utility of TS immunoliposomes in drug delivery.

Mouse monoclonal IgG$_{2a}$ antibody 4.2 against Herpes Simplex Virus (HSV) antigen gD (hereinafter called IgG) was isolated from mouse ascities fluid. IgG was purified by protein A-sepharose affinity chromatography followed by DEAE Sephadex A25 ion-exchange chromatography. The purified antibody was stored in PBS at $-20°$ C. When required, IgG was radiolabelled with $^{125}$I using chloramine T (Hunter and Greenwood, *Nature*, 194: 494-495 (1962)) to a specific activity of $1 \times 10^3$ to $5 \times 10^5$ cpm/micro-g.

In one preferred embodiment of the present invention, the target-sensitive (TS) immunoliposomes directed to glycoprotein D (gD) of HSV were shown as being able to specifically recognize, bind, and become unstable upon binding to the HSV-infected L929 cells. Although these TS immunoliposomes, composed of dioleoyphosphatidylethanolamine (DOPE), where stable at room temperature in PBS, they can become unstable at 37° C. in the presence of serum and divalent cations containing growth media.

Thus in another preferred embodiment of the present invention, there were prepared (from phosphatidyl choline) transphosphatidylated PE (TPE) immunoliposomes which contain a higher degree of saturation of fatty acyl chains. These immunoliposomes composed of TPE were stable in the absence of target membrane and in 10% serum containing tissue culture medium at 37° C. over the time span of these experiments (5-10% destabilization in 48 hr.)

When cells are infected with HSV at a low multiplicity of infection (MOI), only a small fraction of infected cells produce virus that subsequently infects neighboring cells. Additionally, kinetic studies have shown that the virus antigen gD appears at the infected cell surface around 3 hr. after infection, but the release of progeny virions is not detectable until around 8 hr. post infection (PI).

Therefore, it was decided to react virus infected L929 cells with the TS immunoliposomes, directed to gD, at 3 hr. PI. Since these liposomes were stable in the absence of antigen binding, they were not removed from the incubation medium in these experiments. At 42 hr. PI, the supernatant of the L929 cells was collected and titered for the virus yield. The toxicity of the drug on the general cell population was monitored by [$^3$H]dT incorporation since both AraC and ACV inhibit the DNA synthesis. With the low MOI used in these experiments, only a small fraction of cells would be infected with virus and hence, the [$^3$H]dT incorporation assay was mainly a measurement of uninfected cell DNA synthesis.

Figure 7A:
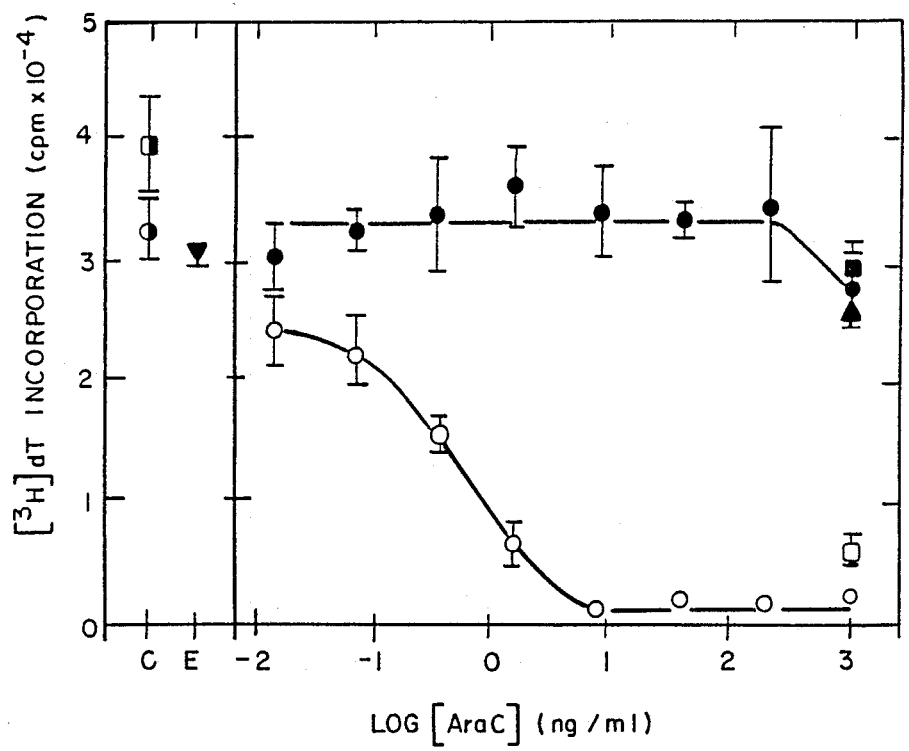
FIGS. 7(A) and (B) compare the effects of free and TS immunoliposomes encapsulated AraC on HSV-infected L929 cells. In these Figures, the following definitions apply.
Figure 7B:
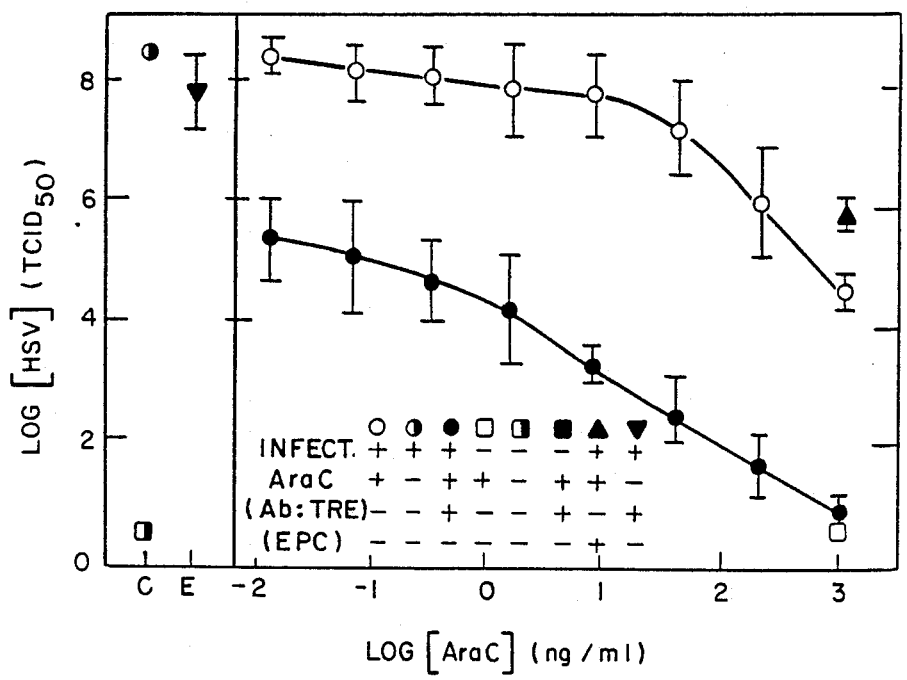

FIGS. 7(A) and (B) compare the effects of free and TS immunoliposome encapsulated AraC (designated Ab:TPE) on HSV-infected L929 cells. Encapsulation of the non-viral-selective drug, AraC, reduced virus production with a 50% effective dose (ED$_{50}$) recorded at 1.8 ng/ml. At least a 1000 fold higher amount of free AraC was required to achieve the same effect (FIG. 7B). While increasing the drug potency, the TS immunoliposomes also reduced the cytotoxicity of AraC to the cell population. Thus, the 50% cytotoxicity (CD$_{50}$) of free AraC was 0.3 ng/ml while the TS immunoliposome entrapped AraC was at least 4 orders of magnitude less toxic (FIG. 7A).

Similarly, FIGS. 8(A) and (B) compare the effects of free and TS immunoliposome encapsulated ACV on HSV-infected L929 cells. The results are in close similarity with those of FIGS. 7(A) and 7(B).

As a control, non-targeted liposomes were prepared from egg phosphatidylcholine (designated EPC). These non-immuno targeted liposomes showed little effect on virus production but this formulation also provided a similar reduction in cell cytotoxicity. Additionally, TS immunoliposome-mediated antiviral activity was due to delivery of the cytotoxic drug. This result further indicated that neutralization of virus by immunoliposome bound antibody was not a major factor in contributing to the therapeutic effect.

No apparent decrease in [$^3$H]dT incorporation by uninfected control cells occurred in the presence of AraC-entrapped TS immunoliposomes providing further evidence for the stability and specificity of these liposomes.

Figure 8B:
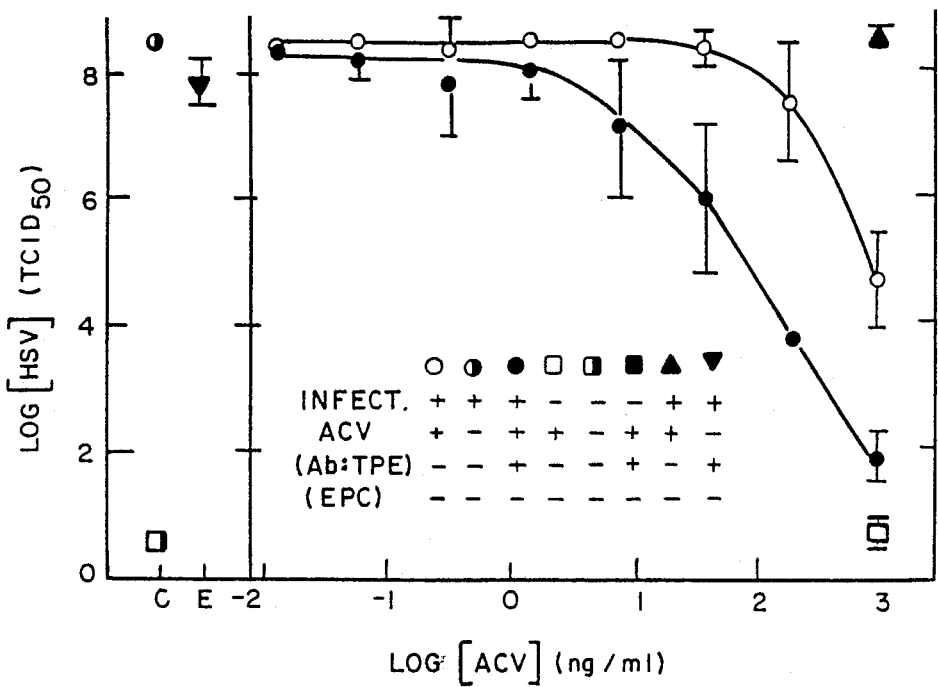

As illustrated in FIGS. 8A and 8B, the preferred liposome-mediated delivery system was further studied for its extension beyond the use of AraC. Thus, parallel experiments were conducted using another nucleoside analog, acyclovir (ACV), a potent and commonly used anti-HSV drug (Swallow et al., British Med. Bull., 41: 322–332 (1984); Balfour, Jr., Ann. Rev. Med., 35: 279–291 (1984)).

As shown in FIGS. 8A and B, a similar but less dramatic effect was observed with TS immunoliposomes containing ACV (designated Ab:TPE) in comparison with the free drug (designated ACV). The $ED_{50}$ was 1.1 micro-g/ml and 125 ng/ml and the $CD_{50}$ was 12.5 ng/ml and 1.4 micro-g/ml for free and TS immunoliposome entrapped ACV, respectively. Additionally, non-targeted liposomes composed of egg phosphatidyl choline (designated EPC) containing ACV on either uninfected cells or infected cells, showed neither antiviral nor toxic effects.

To establish the optimum lipid composition for the preferred target sensitive drug containing immunoliposomes of the present invention, many different liposome formulations were studied for their efficacy at inhibiting virus replication. Among the liposomes tested, AraC-entrapped immunoliposomes composed of transphosphorylated-phosphatidyl-ethanol-amine (TPE) was the most effective at inhibiting virus replication with no apparent cytotoxicity to the virus-infected L929 cells (see FIG. 9B).

Replacing the TPE with egg phosphatidyl-ethanol amine (EPE), which contained a lesser degree of saturation of fatty acyl chain, led to about one order of magnitude reduction in therapeutic effect. Although the immunoliposomes composed of EPC (Ab:EPC, i.e., immunoliposomes which were target insensitive) were slightly more effective than the free AraC, the degree of enhancement in drug potency was about one and a half order of magnitude lower than that of the TPE immunoliposomes.

Nontargeted-EPC liposomes (designated EPC) had little effect on virus yield, but this formulation abolished the cytotoxicity (see FIG. 9A).

Figure 9B:
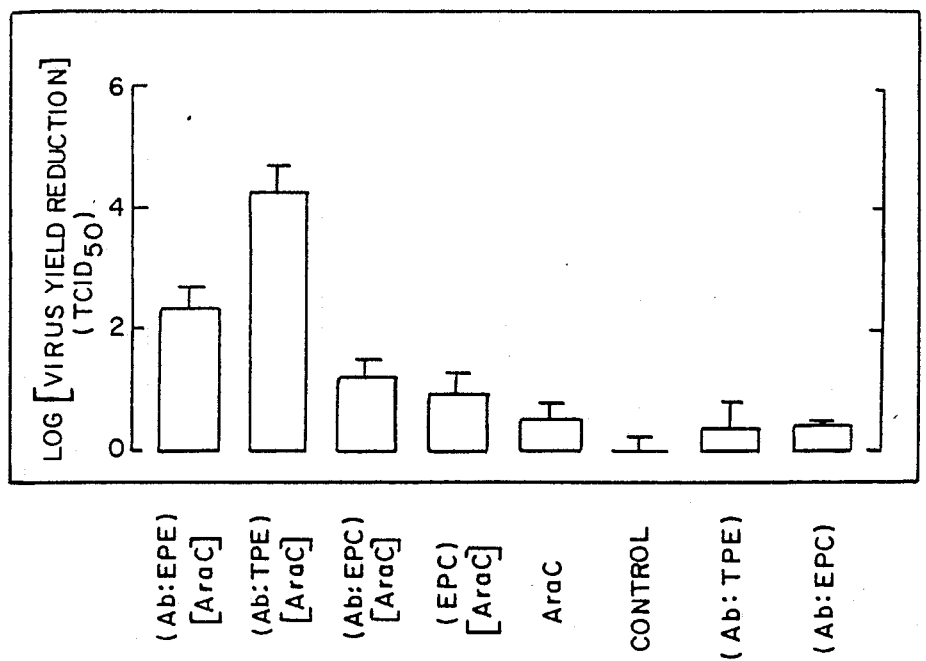

Free AraC introduced at the same concentration of 10 ng/ml was cytotoxic to infected cells (see FIG. 9A) as well as to uninfected cells, while it had only a marginal effect on virus replication (see FIG. 9B).

Based upon these data, AraC entrapped TS immunoliposomes composed of pIgG and TPE were believed to be the most effective formulation at inhibiting virus replication with little or no apparent cytotoxicity to the host cell population.

In order to determine whether the immunoliposomes composed of pIgG and TPE were target sensitive, the L929 cells were infected with various MOI of HSV and the extent of liposome destabilization in tissue culture medium at 37° C. was measured by [$^3$H]AraC released from the immunoliposomes. These data are illustrated in FIG. 10.

As illustrated, the amount of AraC release was MOI dependent. Additionally, under the same conditions, uninfected cells did not cause a detectable [$^3$H]AraC release. Taken together, these data indicate that the immunoliposomes of the present invention composed of TPE maintained the property of target-induced self destabilization upon binding to the preselected virus infected cells.

While not wishing to be bound by theory, it is believed that the surface deposition of TS immunoliposomes was followed by transport of liposome-released drugs into the cytosol via cellular nucleoside transporters. To test this hypothesis, the effect on virus replication of two nucleoside transport inhibitors, p-nitrothiobenzylinosine, and dipyridamole were investigated.

p-Nitrothiobenzylinosine is a competitive inhibitor of the nucleoside transport system with a $K_i$ of 1 nM whereas dipyridamole is a noncompetitive inhibitor of the nucleoside transport system with a $K_i$ of 3 micro-M (Schwenk et al., Biochim. Biophys. Acta, 805: 370–374 (1984); Plagemann et al., Cancer Res., 38: 978–989 (1978)).

As shown in Table II, the addition of either nucleoside transport inhibitor repressed the therapeutic effect of the AraC-encapsulated TS immunoliposomes. A small reduction in virus replication was also noted in the presence of the nucleoside transport inhibitors. Additionally, the repression of therapeutic effect by p-nitrothiobenzylinosine and dipyridamole was concentration dependent. Taken together, these data clearly indicate that TS immunoliposome-mediated cytosolic delivery of AraC, introduced at the surface of infected cells, was mediated by nucleoside transporters.

TABLE II

Repression of Target-Sensitive Immunoliposome Mediated Therapeutic Effects by Nucleoside Transport Inhibitors

| | | Log[HSV][a] | | |
| | | Liposome[b] | | |
| Inhibitor | Concentration | With | Without | Diff. |
| --- | --- | --- | --- | --- |
| None | — | 1.4 ± 0.3 | 7.2 ± 0.5 | 5.8 |
| p-Nitrothio-benzylinosine | 100.0 nM | 3.8 ± 0.4 | 4.6 ± 0.2 | 0.8 |
| | 12.5 nM | 2.8 ± 0.8 | 5.1 ± 0.9 | 2.3 |
| Dipyridamole | 11.1 uM | 3.4 ± 0.4 | 4.8 ± 0.3 | 1.4 |
| | 1.4 uM | 3.7 ± 0.3 | 5.3 ± 0.3 | 1.6 |

[a]Virus yield from the supernatant of HSV - infected cells at 42 hr. PI was determined using the $TCID_{50}$ assay described in Example 14 (infra). These data were the mean S.D. of quadruplicates.
[b]HSV - infected cells were treated with or without 0.1 micro-g/ml (ug/ml) of AraC encapsulated in the TS immunoliposomes.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

REAGENTS

Dioleoyl PE and dioleoyl PC were purchased from Avanti Polar Lipids, Inc. (Birmingham, Ala.). Calcein, and papain were purchased from Sigma Chemical Co. (St. Louis, Mo.). Other reagents were analytical grade.

EXAMPLE 1

Derivatization of IgG with palmitic acid

Coupling of N-hydroxysuccinimide ester of palmitic acid (NHSP) to IgG was done following the procedure of Huang et al., supra.

Briefly, $^{125}$I-labeled IgG was added to the $^3$H-NHSP or NHSP in PBS such that the final deoxycholate (DOC) concentration was 2%.

The coupling was performed at 37° C. for 12 hr. Palmitic acid, the hydrolyzed product of NHSP in the reaction mixture, was separated from derivatized IgG using a Sephadex G75 column and eluted with PBS containing 0.15% DOC as described by Huang et al., supra.

The derivatized IgG was concentrated with a Centricon 30 microconcentrator (Amicon Co., Mass.) and dialyzed against PBS containing 0.15% DOC. Binding activity of palmitoyl-IgG (pIgG) was tested by a radioimmunoassay method using the $^{125}$I-pIgG. Briefly, $4\times10^6$ pfu of HSV in 50 micro-l of PBS pH 7.6 was incubated at 4° C. overnight in an Immulon Removawell (Dynatech Lab Inc.).

After washing, the removawells were incubated with 50 micro-l of 5% goat serum if PBS for 1 hr. to block the nonspecific binding sites. The goat serum was then removed and replaced with $^{125}$I-pIgG (0.1 to 10 micro-l/ml) to 40 micro-l of PBS containing 0.15% DOC. The incubation of pIgG was performed at 4° C. for 1 hr.

After washing with PBS, pH 7.4, the Removawells were counted for $^{125}$I-radioactivity to determine the $^{125}$I-pIgG bound to the HSV adsorbed on the wells. All of the measurements were done in duplicate.

The dissociation constants $K_d$'s were determined by Scatchard analysis (Scatchard, supra).

EXAMPLE 2

Distribution of palmitic acid on pIgG $^3$H-palmitic acid conjugated pIgG (coupling stoichiometry, palmitic acid IgG=2.2) was subjected to papain digestion to prepare Fab and Fc fragments according to Porter, supra. Resulting mixture of Fab and Fc fragments were separated on a 18% SDS-PAGE (Laemmli, *Nature*, 227: 680–685 (1970)).

Gel samples were done in triplicate and the protein bands in two sets of the gel were electrophoretically transferred to nitrocellulose paper for western blot analysis. The third set was stained with Coomassie blue to reveal the protein bands which were then cut out from the dried gel and solubilized in Protosol (NEN Inc.) to determine $^3$H-radioactivity (Nicoli et al., *J. Biochem.*, 249: 2385–2393, (1974)).

After normalizing with respect to the amount of protein and the molecular weight of each band, the distribution of $^3$H-palmitic acid was determined as the percent of total palmitic acid in pIgG. Western blot analysis, see for example, W. N. Burnette, *Anal. Biochem.*, 112: 195–203 (1981), was used to identify the positions of the Fab and Fc bands by using goat anti-mouse-Fab and goat anti-mouse-Fc (Koppel, Inc.), followed by binding of $^{125}$I-protein A and detection with radioautography.

EXAMPLE 3

Liposome preparation

Routinely, PE or PC (1–4 micromole) and a trace amount of hexadecyl $^3$H-cholestanyl ether (CE), Pool et al., *Lipids*, 17 448–452 (1982) (final specific activity 4–11×10$^{13}$ cpm/mole total lipid) were mixed and evaporated free of solvent with a gentle stream of N$_2$ gas.

The dry lipid was vacuum desiccated for a minimum of 30 min. Two hundred micro-l PBS containing varying amounts of derivatized IgG, 0.09% DOC, pH 8.0 was added to hydrate the lipid.

For the liposome lysis experiments, 50 mM calcein was included during the hydration step as a florescence marker. The mixture was sonicated in a bath sonicator (Laboratory Supplies, Inc., Hicksville, N.Y.) for two 5 min. cycles with an intervening 30 min. rest period at room temperature.

The liposome suspension was then chromatographed on a Biogel A-0.5 column to remove the untrapped calcein as well as DOC. The liposomes, eluted with PBS pH 8.0 in the void volume, were detected by $^3$H-radioactivity. These fractions were pooled and stored at 4° C.

In order to determine the concentration-dependent quenching of liposome encapsulated calcein fluorescence, sonicated PC liposomes were prepared in PBS containing various calcein concentrations.

After chromatography to remove the untrapped dye, calcein fluorescence was measured with a Perkin Elmer LS5 spectrophotometer at lambda$_{ex}$=490 nm and lambda$_{em}$=520 nm. Total calcein fluorescence was determined by the addition of DOC to a final concentration of 0.12%. The percent quenching was calculated using the following formula:

$$\% \text{ Quenching} = \left(1 - \frac{F_o}{F_t}\right) \times 100$$

where $F_o$ and $F_t$ are the fluorescence of the liposome samples before and after the addition of DOC. It was found that 50 mM liposome-entrapped calcein gave approximately 70% fluorescence quenching.

EXAMPLE 4

Sucrose density gradient centrifugation

Analytical centrifugation of linear 5–20% sucrose gradient was done as described previously, for example, Huang et al., *J. Biol. Chem.*, 255: 8015–8018 (1980). Briefly, 5 ml of linear 5–20% sucrose gradient in PBS pH 7.4 was overlayed on 0.5 ml of 65% sucrose cushion. Liposome samples were loaded in 200 micro-l and centrifuged in a SW50.1 rotor at 200,000×g for 5 hr. at 4° C. The gradients were fractionated from the bottom using a peristalic pump.

EXAMPLE 5

Infecting L929 cells with viruses

L929 cells were grown as monolayer cultures in 35 mm six-well Linbro plates (Flow Inc.) using McCoy's medium containing 10% fetal calf serum (FCS). Cells were infected with HSV or Sendai with MOI=10 in McCoy's with 2% FCS in 1 ml. After one hour, the infection media was removed and replaced with normal culture media. Incubation was continued at 37° C. for five more hours before the cells were used for the analysis of liposome binding and liposome lysis.

EXAMPLE 6

Binding of immunoliposomes to cells

Virus-infected or normal L929 cells in 35 mm plates were cooled to 4° C. and were incubated in 5% goat serum containing McCoy's medium for 1 hour to block the nonspecific binding sites. Subsequently, immunoliposomes containing $^{125}$I-pIgG and $^3$H-CE in 1 ml were added at various concentrations and incubation continued for 2 hours at 4° C.

In free antibody inhibition experiments, the cells were preincubated with free IgG for 30 min. before the addition of immunoliposomes. After incubation of immunoliposomes with cells, the incubation medium was removed and cells were washed 3 times with 2 ml PBS. The cells were solubilized with 0.5 ml 1% Triton X-100 at room temperature for 2 hr., followed by an additional 0.5 ml Triton wash. The solubilized cells were counted for both $^3$H and $^{125}$I-radioactivity. Measurements were done in duplicate.

EXAMPLE 7

Cell-induced lysis of immunoliposomes

The infected and normal L929 cells were scraped with a rubber policeman and washed three times with PBS. Two micro-l liposomes with entrapped calcein were added to the Linbro Titertek plates containing 20 micro-l of cell suspension in various concentrations and the mixture was incubated at 20° C. for 30 minutes with gently mixing.

After incubation, the liposome-cell suspensions were transferred into a quartz cuvette and the column was brought to 2 ml with PBS. For inhibition experiments, the inhibiting liposomes were added together with the calcein-containing liposomes. The total calcein fluorescence in the incubation mixture was measured after the addition of DOC to a final concentration of 0.12%. The percent dye release was calculated according to:

$$\% \text{ Release} = \frac{F - F_o}{F_t - F_o} \times 100$$

where $F_o$ and $F$ are the calcein fluorescence of the sample before and after the interaction with the cells, respectively. $F_t$ is the total calcein fluorescence after lysis of liposomes with DOC. Light scattering due to cells was less than 1.5% of the total calcein fluorescence. The measurements of calcein fluorescence were reproducible within ±10%.

EXAMPLE 8

Electron microscopy

Immunoliposomes (0.42 micromole/ml) were negatively stained with 0.5% aqueous uranyl acetate and viewed in a Hitachi 600 electron microscope operating at 75 KV. The size of liposomes was determined on photographically enlarged micrographs.

EXAMPLE 9

Papin-induced release of calcein

Immunoliposomes (41 micro-M lipid) with entrapped calcein were added to PBS containing 1 mM EGTA, 1 mM cysteine and various amounts of papain, in a quartz cuvette housed in a temperature controlled cell holder. The initial rate of calcein release was determined as the percent of total fluorescence increase per minute. The temperature of the cell holder was controlled by an Endocal refrigerated circulating water bath (NESLAB Inc., N.H.) with a variation of ±0.5° C.

EXAMPLES 10–16

Materials

Transphosphatidylated phosphatidylethanolamine (from egg phosphatidylcholine) (TPE), egg phosphatidyl ethanolamine (EPE), egg phosphatidylcholine (EPC) were purchased from Avanti Polar Lipids, Inc. (Burmingham, Ala.). (Methyl-$^3$H)-thymidine ([$^3$H]dT) & [$^3$H]acyclovir ($^3$H]ACV) were from ICN Radiochemicals (Irvine, Calif.), and 5-$^3$H]-cytosine- beta-D-arabinoside ([3H]Ara) was from Amersham Co. (Arlington Heights, Ill.). AraC was from Calbiochem (San Diego, Calif.), ACV was from Burroughs Wellcome Co. (Research Triangle Park, N.C.), dipyridamole was from Boehringer Ingleheim Ltd. (Indianapolis, Ind.), p-nitrothiobenzylinosine [S-(p-Nitrobenzyl)-6-thioinosine] was from Aldrich Chemical Co. (Milwaukee, Wis.). Other reagents were analytical grade.

EXAMPLE 10

Antibody Preparation

Isolation and purification of mouse monoclonal IgG$_{2a}$ antibody D4.2 against HSV antigen gD were by conventional procedures. When needed, the purified IgG was acylated with N-hydroxyl succinimide ester of palmitic acid in 20 mole excess of IgG. The acylated palmitoyl IgG (pIgG), in PBS (pH 8.0) containing 0.15% (w/v) deoxycholate (DOC) was separated from the free palmitic acid by Sephadex G75 column chromatography (Huang et al., 1982). This pIgG was previously shown to be the optimum degree of acylation that exhibited efficient membrane incorporation as well as the ability to stabilize the phosphatidylethanolamine (PE) bilayer (Ho et al., Biochem., 25: 5500–5506 (1986).

EXAMPLE 11

Liposome Preparation

About 5–10 micro-mole of lipid was dried and evaporated free of solvent with a gentle stream of N$_2$ gas. The dry lipid was kept under vacuum for a minimum of 30 min. Then appropriate pIgG in 0.15% DOC was added to hydrate the lipid such that the final lipid to protein ratio was 4000:1 (mole/mole). This was followed by the addition of either AraC of ACV to be encapsulated. Finally, the volume was adjusted with phosphate buffered saline (PBS) to contain 1 mg/ml AraC or ACV, 20 mM lipid, and 0.04% DOC. In order to estimate the trapping efficiency of these liposomes, a trace amount of [$^3$H]AraC or [$^3$H]ACV were added when it was necessary. For the liposome used in the target sensitivity assay, the specific activity of [$^3$H]AraC was 4.5×10$^4$ cpm/ug. Then, the mixture was sonicated in a bath sonicator (Laboratory Supplies, Inc., Hicksville, N.Y.) for two 5-min. cycles with an intervening 30-min. rest period as described previously (Ho et al., supra).

The resulting translucent liposome suspension was chromatographed on a Bio-Gel A-0.5m column at a flow rate of 0.3 ml/min. to remove the untrapped drugs as well as DOC. Liposome fractions, eluted in the void volume were pooled and extruded through the 0.2 micron sterile filter (Gelman Sciences, Ann Arbor, Mich.) for sterilization. Analysis of a small fraction of extruded liposome suspension by Bio-Gel A-0.5m chromatography showed that no apparent release of the drugs from liposomes due to extrusion. Assuming 90% recovery from the chromatography, the trapping efficiency of these liposomes was determined using the $^3$H] marker of AraC and ACV to be about 1.2 micro-l per micro-mole of lipid.

EXAMPLE 12

Virus

The HF strain of HSV-1 was propagated on Hep-2 cell. After 3 cycles of freeze and thawing of the virus infected cells, the virus released were isolated from the supernatant after palleting the cell debris at 1000 g for 10 min. These virus stock contained $1 \times 10^8$ pfu/ml and were stored in $-70°$ C.

EXAMPLE 13

Infecting L929 Cells with HSV

L929 cells at 75–80% confluency in 96-well Coster plates were infected with 0.1 multiplicity of infection (MOI) in McCoy's medium with 2% CS for 1 hr. Then the infection medium was removed and replaced with McCoy's medium containing 10% CS. For the target sensitivity assay (see below), L929 cells were grown in 35-mm six-well Linbro plates and a similar procedure was used to infect the L929 cell with various concentration of HSV, ranging from 0–10 MOI.

EXAMPLE 14

Efficacy of Liposome in Inhibiting Virus Replication

HSV-infected L929 cells in 7-mm 96-well plates were used in these experiments and each experiment was performed in quadruplicate. At 3 hr. post infection (PI), the growth medium of infected or uninfected cell was removed, and replaced with 180 micro-l of either liposome-entrapped or free drug AraC or ACV containing medium.

In the experiments where nucleoside-transport inhibitors were used, the inhibitors were added at 30 min. prior to the AraC-entrapped liposome addition. Inhibitors were present throughout the assay. For the control experiments, the infection medium was replaced with the fresh growth medium. At 6 hr. PI, 1 micro-Ci of [$^3$H]dT was added in 20 micro-l for cytotoxicity assay (see below). Then incubation continued at 37° C. in a $CO_2$ incubator. At 42 hr. PI, the growth medium was removed and immediately titered for the virus yield using the 50% tissue culture infective dose ($TCID_{50}$) assay using Vero cells. The TCID50 assay was done in quadruplicates and the results were expressed in average $\pm$S.D.

EXAMPLE 15

L929 Cell Toxicity Assay

Cytotoxicity of the L929 cells was determined by labeling the cells at 6 hr. PI with [3H]dT. At 42 hr. PI, the growth medium was removed and the cells were washed with cold PBS for a total of three times. Then the DNA was precipitated with 5% trichloroacetic acid (TCA) at 4° C. After two cycles of 2 hr. incubation with fresh TCA, the precipitates at the bottom of the plates were washed one more time with 200 micro-l of fresh TCA. Finally, the precipitates were redissolved and dequenched with 1N NaOH overnight. The solubilized TCA precipitates were counted for tritium radioactivity. Data presented were the average $\pm$S.D. of the quadruplicates.

EXAMPLE 16

Target Sensitivity of Immunoliposomes Composed of TPE

L929 cells infected with various MOI in six-well plates were used in these experiments. Quadruplicates samples were used for each MOI. At 6 hr. PI, the growth medium was removed and replaced with 1 ml of 0.898 micro-g [3H]AraC (specific activity=$4.5 \times 1^{-4}$ cpm/ug) in McCoy's medium containing 10% CS. After 30 min. incubation in a $CO_2$ incubator at 37° C., the supernatant was removed and determined the [$^3$H]AraC released into the medium. This was done by separating the free and liposome associated AraC in the supernatant collected. Total amount of [$^3$H]AraC recovered in the cell supernatant ranged from 64 to 90 percent of the amount added. Three hundred micro-l of the cell supernatant was loaded on a 1 ml spun column containing Sephadex G25 (superfine). The recovery of liposome entrapped AraC from the G-25 column using the control liposomes was 28 percent. After correcting for recovery of the G-25 spun-column, the percent of total AraC was determined as follows:

$$\% \text{ of Total} = [1 - AraC_r/AraC_t] \times 100$$

Where $AraC_r$ was the corrected value of liposome associated [$^3$H]AraC recovered in the void volume, and $AraC_t$ was the total [$^3$H]AraC which included free and liposome associated associated AraC. These experiments were done in quadruplicate and presented as average $\pm$S.D.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. Target sensitive immunoliposomes consisting essentially of phosphatidylethanolamine and a stabilizing amount of fatty acid ($C_{12}$ to $C_{24}$) derivatized antibody, said antibody having an affinity for the target cell surface which immunoliposomes release their entrapped contents upon binding to a target cell surface.

2. The target sensitive immunoliposomes of claim 1, wherein the phosphatidylethanolamine is selected from the group consisting of dioleoyl phosphatidylethanolamine and transphosphotidylated phosphtidylethanolamine.

3. The target sensitive immunoliposomes of claim 1, wherein the fatty acid is a palmitic acid derivative.

4. The target sensitive immunoliposomes of claim 1, wherein the antibody is IgG.

5. The target sensitive immunoliposomes of claim 1, wherein the antibody is a monoclonal antibody.

6. The target sensitive immunoliposome of claim 5, wherein the monoclonal antibody recognizes the glycoprotein D of the Herpes Simplex Virus (HSV).

7. The target sensitive immunoliposomes of claim 1, wherein the entrapped contents consist essentially of a pharmaceutically acceptable drug.

8. The target sensitive immunoliposomes of claim 7, wherein the pharmaceutically acceptable drug is selected from the group consisting of cytotoxic and antiviral drugs of the nucleoside analog family.

9. The target sensitive immunoliposomes of claim 8, wherein the cyclotoxic and antiviral drugs are selected from the group consisting of fluorodeoxy uridine, iododeoxyuridine, acyclovir and cytosine arabinoside.

10. The target sensitive immunoliposomes of claim 7, in a form suitable for injection.

11. The target sensitive immunoliposomes of claim 7, in a form suitable for ophthalmic application.

12. The target sensitive immunoliposomes of claim 7, in a form suitable for topical applications.

13. The target sensitive immunoliposomes of claim 1, further consisting essentially of palmitoyl IgG and phosphaticlethanolamine in a molar ratio of not less than $2.5 \times 10^{-4}$.

14. The target sensitive immunoliposomes of claim 10, wherein the minimal coupling stoichimetry of palmitic acid to antibody is 2.2.

15. A method of delivering therapeutic agents to the surface of cells in need of such treatment comprising the steps of:
   (a) forming target sensitive immunoliposomes from phosphatidylethanolamine and a stabilizing amount of fatty acid ($C_{12}$ to $C_{24}$) derivatized antibody, said antibody having an affinity for the target cell surface;
   (b) entrapping one or more therapeutic agents within the immunoliposomes of step (a); and
   (c) administering the immunoliposomes prepared in step (b) to a patient in need of such treatment.

16. The method of claim 15, wherein the phosphatidylethanolamine is selected from the group consisting of dioleoyl phosphatidylethanolamine and transphosphotidylated phosphatidylethanolamine.

17. The method of claim 15, wherein the fatty acid is a palmitic acid derivative.

18. The method of claim 15, wherein the antibodys is IgG.

19. The method of claim 15, wherein the antibody is a monoclonal antibody.

20. The method of claim 19, wherein the monoclonal recognizes the glycoprotein D of the Herpes Simplex Virus (HSV).

* * * * *